*(12)* United States Patent
Collet et al.

*(10)* Patent No.: US 12,090,239 B2
*(45)* Date of Patent: Sep. 17, 2024

(54) APPARATUS AND METHOD FOR ULTRAVIOLET DISINFECTION

(71) Applicant: Blu Perspective LLC, Portage, MI (US)

(72) Inventors: Corbin Collet, Portage, MI (US); April Jennesis-Collet, Kalamazoo, MI (US); Brian Brandon, Bellevue, MI (US)

(73) Assignee: Blu Perspective LLC, Portage, MI (US)

( * ) Notice: Subject to any disclaimer, the term of this patent is extended or adjusted under 35 U.S.C. 154(b) by 1 day.

(21) Appl. No.: 17/702,997

(22) Filed: Mar. 24, 2022

(65) Prior Publication Data

US 2022/0305159 A1    Sep. 29, 2022

Related U.S. Application Data

(60) Provisional application No. 63/165,452, filed on Mar. 24, 2021.

(51) Int. Cl.
*A61L 2/10* (2006.01)
*F21V 21/005* (2006.01)
*F21Y 115/10* (2016.01)

(52) U.S. Cl.
CPC ............ *A61L 2/10* (2013.01); *F21V 21/005* (2013.01); *F21Y 2115/10* (2016.08)

(58) Field of Classification Search
CPC ....... A61L 2/10; F21V 21/005; F21Y 2115/10
See application file for complete search history.

(56) References Cited

U.S. PATENT DOCUMENTS

| | | | |
|---|---|---|---|
| 8,473,097 B2 * | 6/2013 | Shoenfeld | A61L 2/10 221/92 |
| 8,481,985 B2 | 7/2013 | Neister | |
| 8,753,575 B2 | 6/2014 | Neister | |
| 8,975,605 B2 | 3/2015 | Neister | |
| 9,700,642 B2 | 7/2017 | Neister | |
| 10,398,000 B2 | 8/2019 | Rantala | |
| 2008/0236183 A1 * | 10/2008 | Iimura | G02B 6/001 62/264 |
| 2014/0131595 A1 * | 5/2014 | Nathan | A61L 2/0047 250/504 R |
| 2016/0154170 A1 * | 6/2016 | Thompson | B60Q 3/225 362/555 |

(Continued)

*Primary Examiner* — Abdulmajeed Aziz
*Assistant Examiner* — Jessica M Apenteng
(74) *Attorney, Agent, or Firm* — Gardner, Linn, Burkhart & Ondersma LLP

(57) ABSTRACT

A disinfection chamber for disinfecting objects placed within an interior space of the disinfection chamber. The chamber includes a plurality of LED fixtures and one or more shelves. The LED fixtures each comprise LED ultraviolet sources and at least one LED visible light source. The ultraviolet sources are configured to emit germicidal ultraviolet light. Each of the shelves comprise a grill frame configured to support and position objects. A first shelf of the one or more shelves is positioned at or near a floor of the interior space. A first LED fixture is positioned upon the first shelf and beneath the grill frame. A second LED fixture is positioned at or near a ceiling of the interior space. The first and second LED fixtures are arranged within the interior space, such that objects placed within the interior space will be disinfected by the ultraviolet sources.

20 Claims, 16 Drawing Sheets

(56) References Cited

U.S. PATENT DOCUMENTS

| | | | |
|---|---|---|---|
| 2017/0290934 A1* | 10/2017 | Dobrinsky | G02B 19/0095 |
| 2018/0243458 A1* | 8/2018 | Shatalov | A61L 9/20 |
| 2018/0353629 A9 | 12/2018 | Neister et al. | |
| 2020/0030469 A1 | 1/2020 | Neister et al. | |

* cited by examiner

FIG. 2A

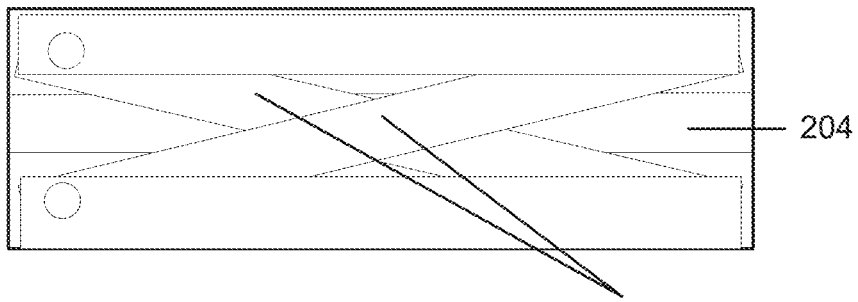

Scissor arms 210 of height adjustment mechanism 202.

FIG. 2B

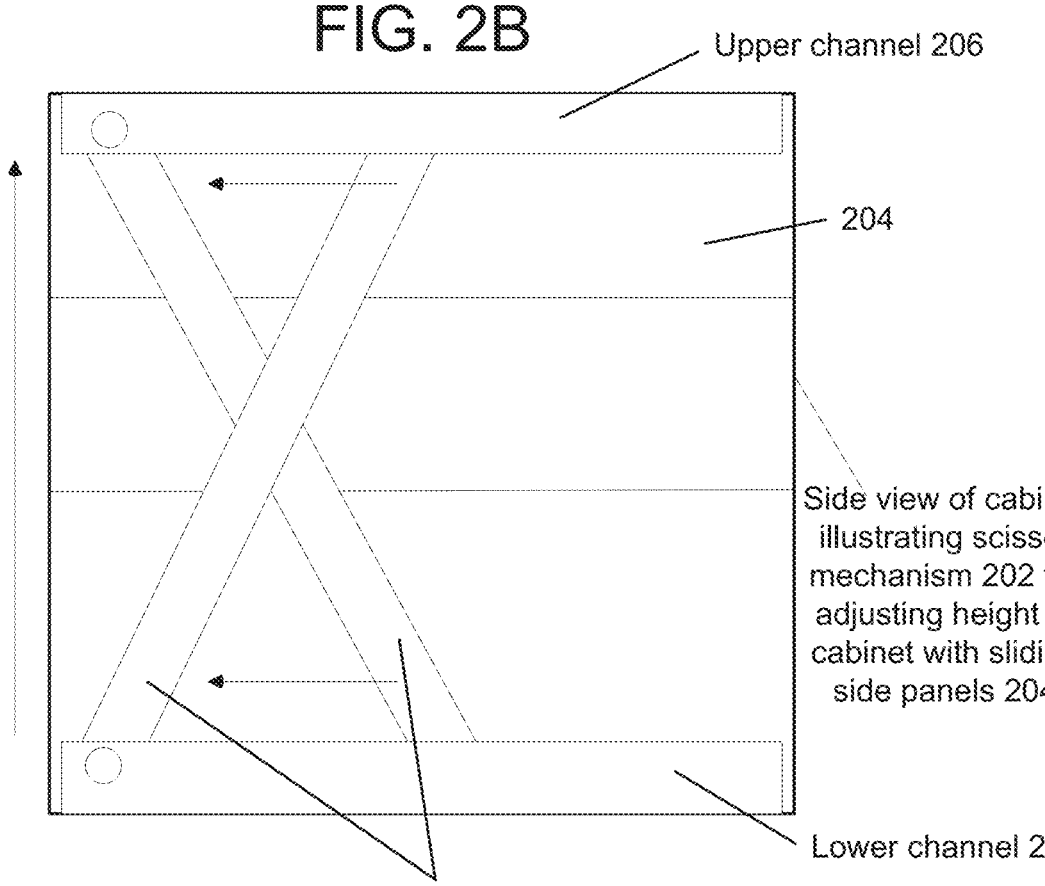

Upper channel 206

204

Side view of cabinet illustrating scissor mechanism 202 for adjusting height of cabinet with sliding side panels 204

Lower channel 208

Scissor arms 210 of height adjustment mechanism 202. As scissor arms 210 are drawn together along channels 206, 208 and the channels 206, 208 are subsequently pushed away from each other, the height of the cabinet is raised as the side panels 204 slide.

1705a

1704a

APPARATUS AND METHOD FOR ULTRAVIOLET DISINFECTION

CROSS REFERENCE TO RELATED APPLICATIONS

The present application claims the filing benefits of U.S. provisional application, Ser. No. 63/165,452, filed Mar. 24, 2021, which is hereby incorporated by reference herein in its entirety.

FIELD OF THE INVENTION

The present invention is directed to ultraviolet sanitation, and in particular, to using ultraviolet light to disinfect air and surfaces.

BACKGROUND OF THE INVENTION

Conventional ultraviolet light sources, such as ultraviolet C (UV-C) light bulbs or light fixtures, have been used to disinfect surfaces. UV-C wavelengths typically used for disinfecting include, for example, 222 nm and 254 nm. UV light sources are usually positioned so that when energized, they emit ultraviolet light to disinfect surfaces exposed to the ultraviolet light.

SUMMARY OF THE INVENTION

Embodiments of the present invention provide a system, apparatus, and methods for disinfecting the interior of a disinfection chamber. The disinfection chamber includes at least two LED fixtures, a first LED fixture positioned at or near a floor of the disinfection chamber and a second LED fixture positioned at or near a ceiling of the disinfection chamber. The disinfection chamber includes a shelf with a grill frame configured to position objects for disinfection. The first LED fixture is positioned upon the shelf and beneath the grill frame. The pair of LED fixtures are positioned such that when one or more objects are placed upon the grill frame, the pair of LED fixtures will disinfect the objects placed within an interior space of the disinfection chamber. The LED fixtures include LED ultraviolet sources, which are configured to disinfect the air within the disinfection chamber, and anything positioned within the interior space of the disinfection chamber. Additional shelves may be placed within the interior space of the disinfection chamber such that multiple shelves are provided. Each of the additional shelves includes a pair of LED fixtures, a top set of LED fixtures positioned upon a top surface of the shelf, and under respective grill frames, and a lower set of LED fixtures positioned upon a bottom surface of the shelf. Each of the LED fixtures includes LED ultraviolet sources for emitting germicidal ultraviolet light. The LED ultraviolet sources are configured to emit ultraviolet light onto surrounding surfaces within the interior space of the disinfection chamber. The LED fixtures also include LED light sources configured to emit visible light. A first set of LED light sources of the LED fixtures are used as work lights within the interior space of the disinfection chamber, e.g., white LED lights. A second set of LED light sources are used to indicate whether the LED ultraviolet sources are emitting ultraviolet light.

In an aspect of the present invention, a disinfection chamber is provided for disinfecting objects placed within the interior space of the disinfection chamber. The chamber includes at least two LED fixtures and a shelf that includes a grill frame configured to support and position objects for disinfection. Each of the LED fixtures includes an arrangement of LED ultraviolet sources, and at least one LED light source. The shelf is positioned at or near a floor of the disinfection chamber. A first LED fixture of the at least two LED fixtures is positioned upon the shelf and beneath the grill frame. A second LED fixture of the at least two LED fixtures is positioned at or near a ceiling of the disinfection chamber. The first and second LED fixtures are arranged within the interior space of the disinfection chamber such that objects, as well as the air within the chamber, will be disinfected by LED ultraviolet sources of the first and second LED fixtures. Each of the LED fixtures includes LED ultraviolet sources configured to emit germicidal ultraviolet light. The LED ultraviolet sources are configured to emit ultraviolet light onto surrounding surfaces within the interior space of the disinfection chamber. Each of the LED fixtures also includes LED light sources configured to emit visible light. A first set of LED light sources of the LED fixtures are used as work lights within the disinfection chamber, e.g., white LED lights. A second set of LED light sources are used to indicate whether the LED ultraviolet sources are emitting ultraviolet light.

In a further aspect of the present invention, the disinfection chamber includes multiple shelves. Each additional shelf includes a pair of LED fixtures, a top set of LED fixtures positioned upon a top surface of the shelf, and under respective grill frames, and a lower set of LED fixtures positioned upon a bottom surface of the shelf.

The disinfection chamber may also include a collapsible cabinet housing such that the disinfection chamber has an adjustable height, with the cabinet housing height set with a pair of scissor arms arranged on either side of the cabinet housing of the disinfection chamber.

The disinfection chamber may also be mobile and powered via a 12V DC power source. The disinfection chamber also includes a control module and sensors, which include at least one proximity sensor and at least one infrared sensor. The control module will control the operation of the LED ultraviolet sources. The control module is configured to control the LED ultraviolet source as defined by the signal outputs of the sensors.

In an aspect of the present invention, the LED ultraviolet source is configured to emit ultraviolet C (UV-C) light. UV-C light sources include exemplary 260-280 nm LED fixtures and exemplary 254 nm mercury lamp fixtures.

In yet another aspect of the present invention, the LED ultraviolet source includes one or more 260-280 nm light emitting diodes (LEDs). In a further aspect of the present invention, alternative ultraviolet sources may include one or more ultraviolet sources, such as 222 nm or 254 nm incandescent light fixtures, 222 nm or 254 fluorescent light fixtures, or 222 nm excimer light fixtures.

Thus, a mobile disinfection chamber, powered by a low voltage DC power source may be provided for disinfecting objects placed within the interior space of the disinfection chamber. The disinfection chamber includes a plurality of ultraviolet source devices, a first ultraviolet source positioned at or near a floor of the disinfection chamber and a second ultraviolet source positioned at or near a ceiling of the disinfection chamber. The first and second ultraviolet sources are configured to disinfect the air within the disinfection chamber, and anything positioned within the disinfection chamber.

These and other objects, advantages, purposes, and features of the present invention will become apparent upon review of the following specification in conjunction with the drawings.

BRIEF DESCRIPTION OF THE DRAWINGS

FIGS. 2A and 2B illustrate side views of an exemplary adjustment mechanism for a disinfection chamber with adjustable height side walls in accordance with the present invention;

DESCRIPTION OF THE PREFERRED EMBODIMENTS

Figure 1:
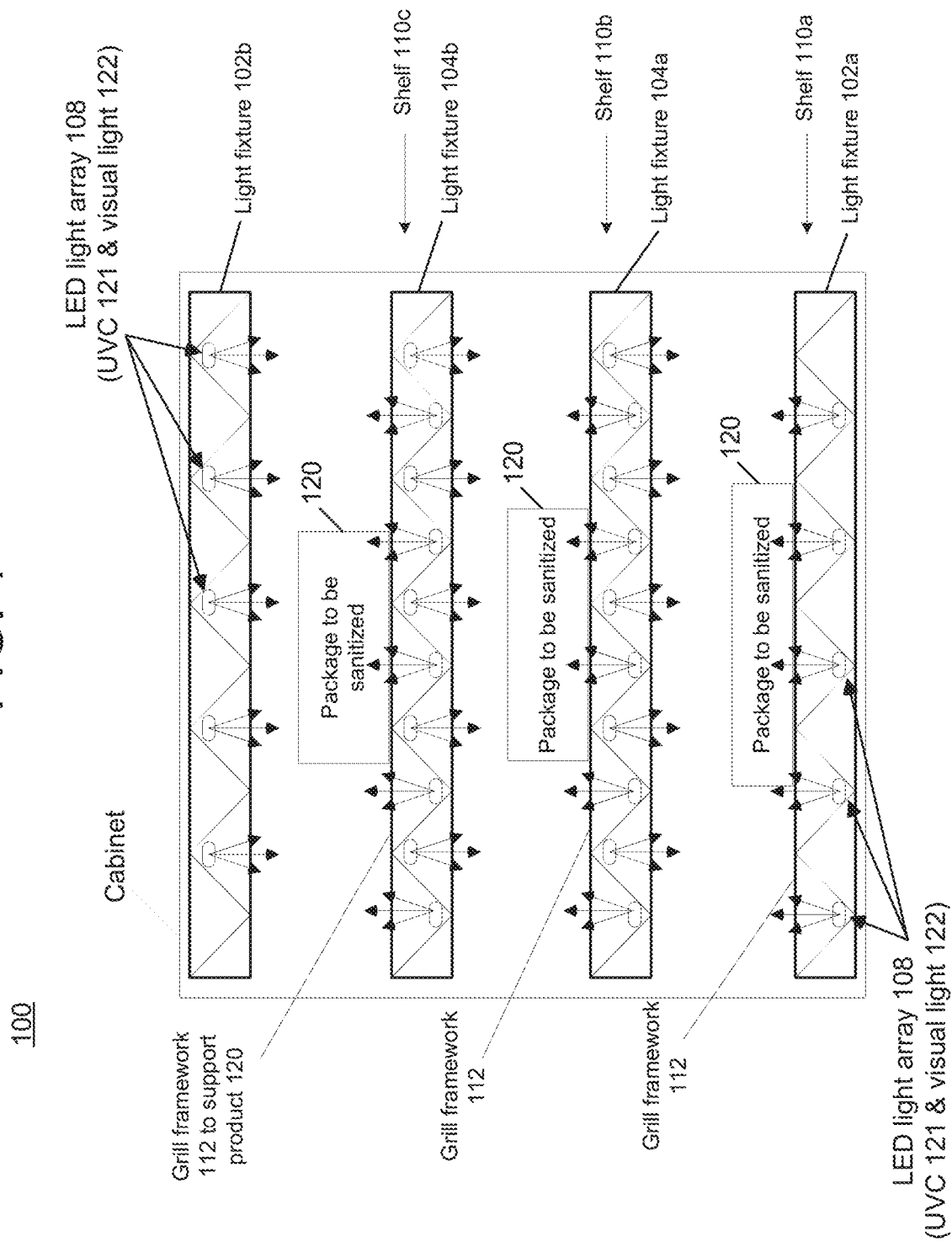
FIG. 1 is a side view of an exemplary disinfection chamber for disinfecting objects placed within the interior space of the disinfection chamber in accordance with the present invention.

Referring to the drawings and the illustrative embodiments depicted therein, a mobile disinfection chamber provides mobile disinfection services of objects. The mobile disinfection chamber is powered via a low-voltage DC power source. Ultraviolet sources are mounted within an interior space of the disinfection chamber and arranged such that objects placed within the disinfection chamber may be adequately exposed to antimicrobial ultraviolet light. The disinfection chamber may include adjustable height walls such that the disinfection chamber may be placed within a space and fitted to that space. The ultraviolet sources are configured to emit ultraviolet light, e.g., ultraviolet C (UV-C) light, which disinfects those surfaces that are reached by the ultraviolet light. The apparatus may comprise two or more ultraviolet light sources, with the ultraviolet light provided by light emitting diodes (LEDs). Optionally, other ultraviolet light sources may be used, including one or more incandescent bulbs or light fixtures, excimer light fixtures, as well as any other light fixture capable of emitting ultraviolet light. Because the disinfecting apparatus is configured for mounting within a space, such as within a vehicle, the disinfection chamber includes an adjustable height for filling the dimension of the space. As also discussed herein, the disinfection chamber may be incorporated into a vehicle or configured as standalone units.

The ultraviolet sources of the disinfection chamber may comprise one or more ultraviolet light fixtures. While the disinfection chamber described herein utilizes arrays of LED ultraviolet sources, other ultraviolet sources may also be used. For example, the LED fixtures may utilize other ultraviolet sources, such as one or more fluorescent light fixtures, excimer light fixtures, or incandescent light fixtures, which may be arranged as one or more linear ultraviolet light fixtures or arranged in linear arrays of ultraviolet light fixtures. UV-C LEDs may be configured to emit ultraviolet light at a wavelength range of 260-280 nm, while UV-C mercury lamps may be configured to emit ultraviolet light at a wavelength of 254 nm. UV-C excimer light fixtures may be configured to emit ultraviolet light at a wavelength of 222 nm. Meanwhile, UV-C fluorescent light fixtures may be configured to emit ultraviolet light at a wavelength of 222 nm or 254 nm. Other wavelengths within the ultraviolet C light range used for ultraviolet antimicrobial treatment are also possible. For example, UV-C wavelengths are those wavelengths between 100 nm to 280 nm, such as those wavelengths between 222 nm to 280 nm. Those selected wavelengths discussed above are particularly germicidal in that they damage the DNA of microorganisms (e.g., bacterium, viruses, and other pathogens) which prevents the microorganisms from reproducing. When the ultraviolet sources arranged within the interior space of the disinfection chamber are energized, objects placed within the disinfection chamber's interior and the interior surfaces of the chamber will be exposed to the combined ultraviolet light emitted by the ultraviolet sources.

Figure 3A:
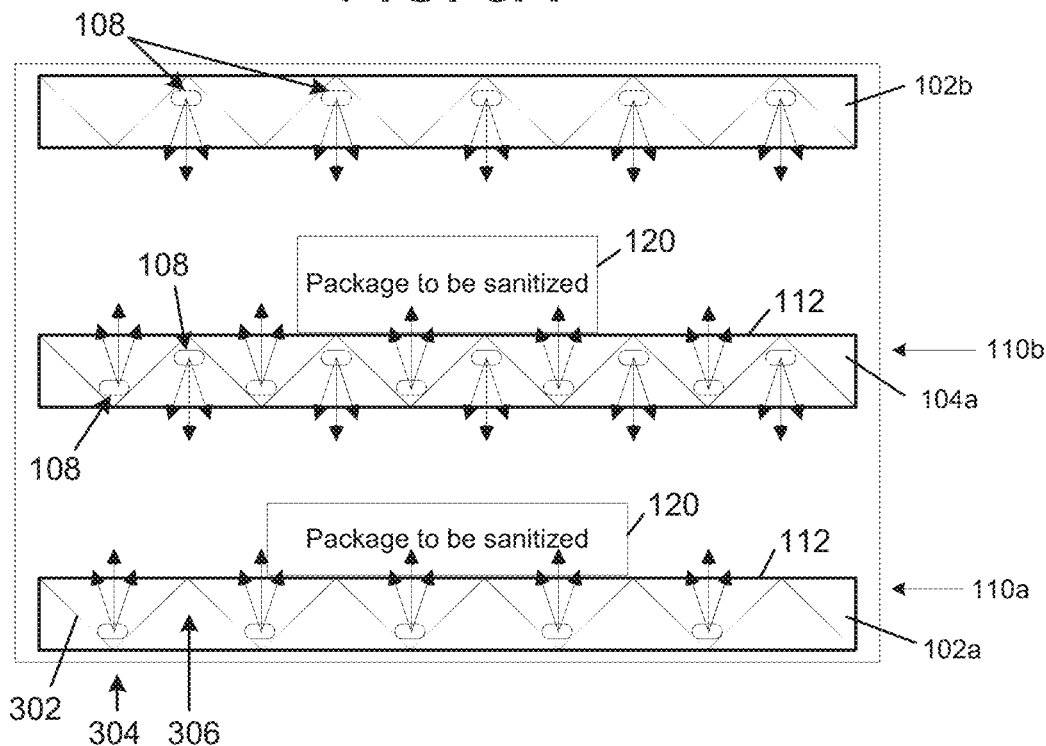
FIG. 3A is a side view of the disinfection chamber of FIG. 1 arranged with only a single middle shelf in accordance with the present invention.
Figure 3B:
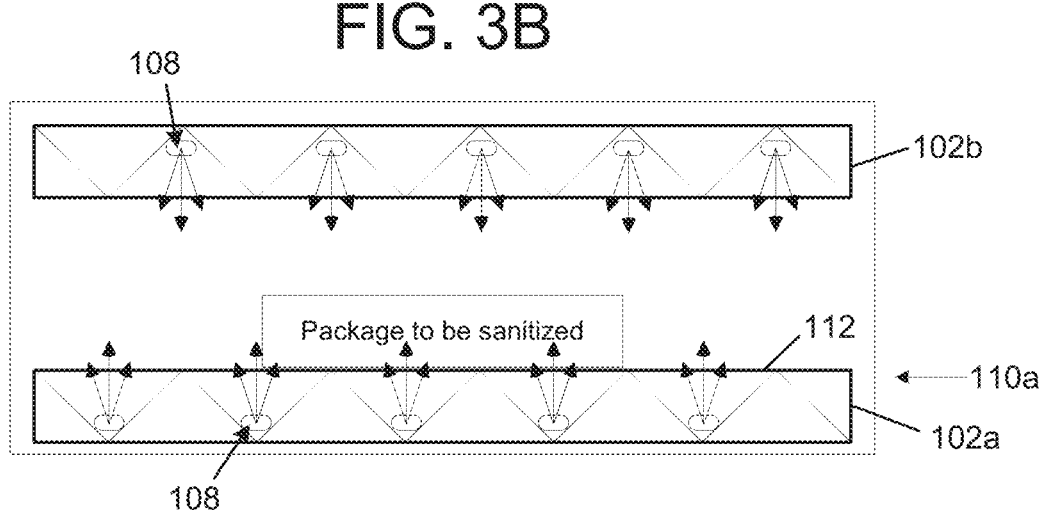
FIG. 3B is a side view of the disinfection chamber of FIG. 1 arranged without any middle shelfs in accordance with the present invention.

FIG. 1 illustrates the interior of an exemplary disinfection chamber 100. As illustrated in FIG. 1, a light fixture 102*a* is arranged at or near the floor of the disinfection chamber 100, while an opposite light fixture 102*b* is arranged at or near the ceiling of the disinfection chamber 100. LED light arrays 108 of the LED light fixture 102*a* project upward, while LED light arrays 108 of the light fixture 102*b* project downward. As illustrated in FIG. 1, the disinfection chamber 100 includes shelves 110 for positioning objects 120 for disinfecting. The middle shelves 110*b-c* are formed from double-sided light fixtures 104*a-b*, while a lowest shelf 110*a*, positioned on the bottom of the disinfection chamber 100, is formed from the lower light fixture 102*a*. Each of the shelves 110*a-c* includes a grill framework 112. While FIG. 1 illustrates a pair of middle shelves 110*b*, 110*c* (formed from the pair of light fixtures 104*b*, 104*a*), FIGS. 3A and 3B illustrate a disinfection chamber with a single middle shelf 110*b* and no middle shelf, respectively. As illustrated in FIGS. 1 and 3A, each middle shelf 110 includes a double-sided light fixture 104 and a grill framework 112. The LED light arrays 108 of the double-sided light fixtures 104 are arranged to project in opposite directions.

Figure 12A:
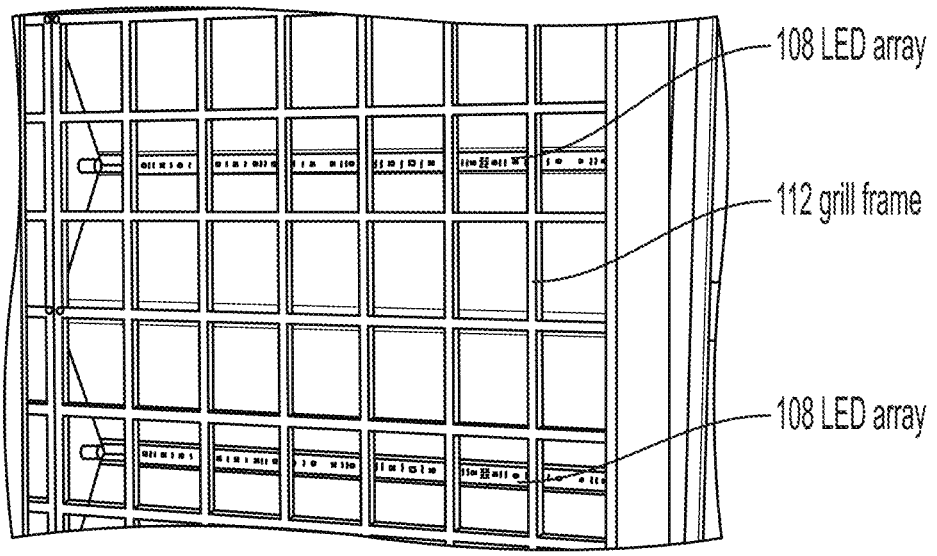
FIG. 12A is perspective view of a portion of one of the LED fixtures of the disinfection chamber of FIG. 4 illustrating linear arrays of LED devices and a grill frame for positioning an object in accordance with the present invention.
Figure 12B:
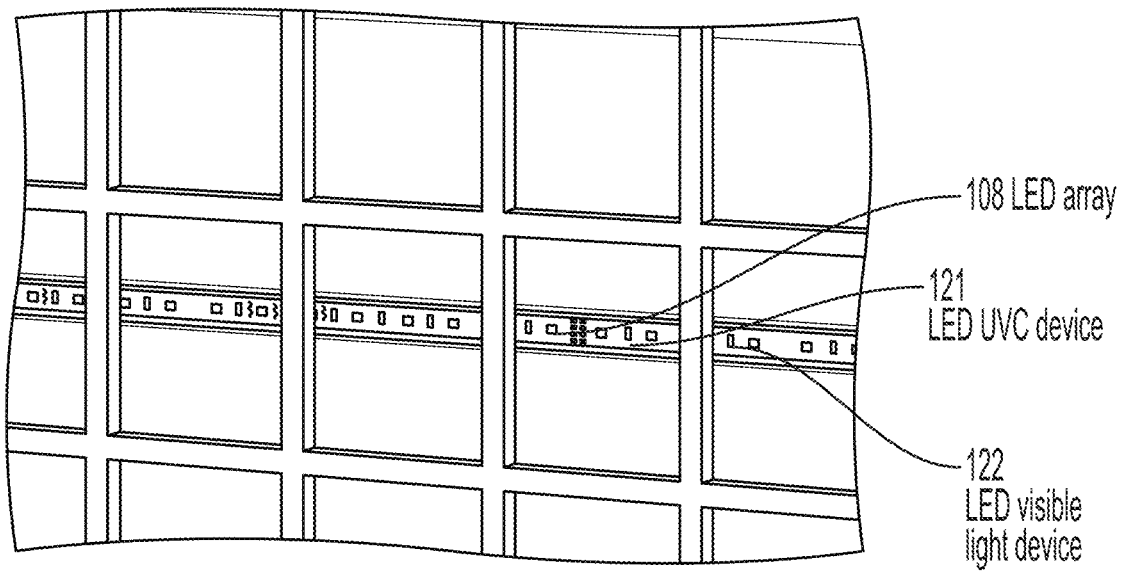
FIG. 12B is a perspective view of a linear array of LED devices and grill frame of FIG. 12A illustrating LED ultraviolet sources and LED visible light sources in accordance with the present invention.

As illustrated in FIGS. 1, 3A, 4, 5, 8, and 9, each light fixture 102, 104 is configured with a W-shaped reflector 302 comprising a series of alternating peaks 304 and valleys 306 (see FIG. 3A). As illustrated, a respective LED array 108 is positioned within a separate valley or trough 306 of the shelf 110. The valleys or troughs 306 of the W-shaped reflector 302 are configured to reflect and direct the ultraviolet light to aid in distributing the ultraviolet light when the ultraviolet light sources (of the LED arrays 108) are emitting. Furthermore, the design and shape of the W-shaped reflector 302 within each light fixture 102, 104 is configured to achieve a minimum-desired general reflectivity that achieves a required fluency (i.e., total radiant energy reaching a particular point), such that a sufficient "UV dose" is reaching an object 120 such that the object 120 will be adequately sanitized during a sanitization cycle. Note that with the middle shelves 110*b-c*, the peaks 304 or valleys 306 of one side of the W-shaped reflector 302 form the opposing valleys 306 or peaks 304 of the opposite side of the W-shaped reflector 302, such that a desired fluency or UV dose for the ultraviolet light is maintained even when multiple shelves 110 are utilized within the disinfection chamber 100. Note that the bottom light fixture 102*a* and the top light fixture 102*b* do not include opposing LED light arrays (the LED light arrays 108 are arranged to project upwards or downwards only). As also discussed herein, each LED array 108 includes LED ultraviolet light sources 121 and LED visible light sources 122 (see FIG. 12B). The LED visible light sources 122 are used as work lights (e.g., white light LEDs) or as indicator lights when the ultraviolet light sources 321 are emitting (e.g., blue light LEDs or other colors) (see FIG. 17).

FIGS. 2A and 2B illustrate an adjustable height disinfection chamber 200 with an exemplary height adjustment mechanism 202 (the disinfection chamber has adjustable height sidewalls 204 (see FIG. 2B, where three sidewalls 204 are sliding apart as the height of the chamber 200 is raised). As illustrated in FIG. 2A, the adjustable-height chamber 200 may be collapsed when not in use or when travelling, and then as illustrated in FIG. 2B, raised to a desired height for use. As illustrated in FIG. 2B, sets of scissor arms 210 on either side of the adjustable height disinfection chamber 200 are configured to control the height of the chamber 200. As the scissor arms 210 are drawn together along channels 206, 208, with a channel 206, 208 positioned on either side of a top and bottom of the adjustable-height chamber 200, the pairs of upper and lower channels 206, 208 of the adjustable-height disinfection chamber 200 are pushed away from each other and the height of the chamber 200 is raised. FIGS. 2A and 2B illustrate an exemplary scissor mechanism 202 (including the scissor arms 210 and channels 206, 208) for adjusting the height of the disinfection chamber 200.

Figure 17:
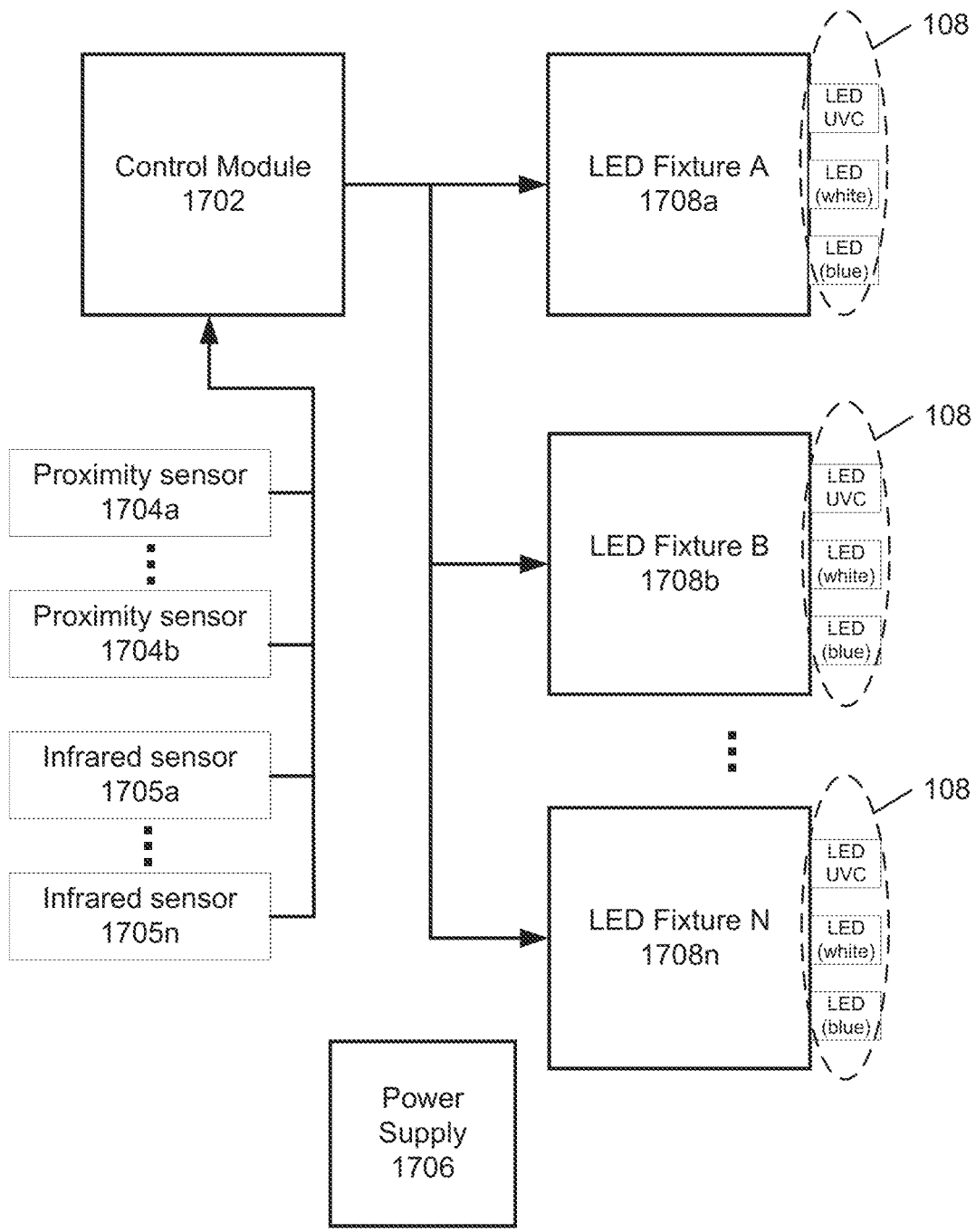
FIG. 17 is a block diagram of an exemplary disinfection system illustrating a control module communicatively coupled to proximity/infrared sensors for controlling the operation of LED fixtures in accordance with the present invention.

FIGS. 4-9 illustrate several views of an exemplary disinfection chamber 400. The disinfection chamber 400 is contained within a cabinet housing 402, formed with a set of cabinet panels 406 and a roll-down door 404 that is pulled down into position before using the disinfection chamber 400. Whether a roll-down door 404 or other means for closing the chamber 400, once the chamber 400 is secured, objects 120 placed upon the grill frames 112 of the shelves 410 within the interior space of the disinfection chamber 400 will be sanitized. Like the disinfection chamber 100 of FIG. 1, the disinfection chamber 400 includes a top-mounted light fixture (not shown) and a bottom-mounted light fixture 102*a*, and with the light fixture 102*a* part of a shelf 110*a* that includes a grill framework 112. The disinfecting process may be controlled with a control module. FIG. 17 illustrates a control module 1702 configured to control the duration of a "disinfection cycle" as well as the intensity of the ultraviolet light emitted. As discussed herein, the control module 1702 uses proximity and/or infrared sensors 1704*a-n* to ensure the door 404 is closed before beginning the disinfecting process. The control module 1702, LED visible lights 122, and ultraviolet sources 121 (e.g., LED UVC ultraviolet sources) are powered via a single low-voltage DC power source 1706, such as, a 12V DC power source. In one embodiment, the 12 V DC power source 1706 is a battery. In another embodiment, the 12V DC power source 1706 is provided by a vehicle's 12V DC power source.

Figure 10A:
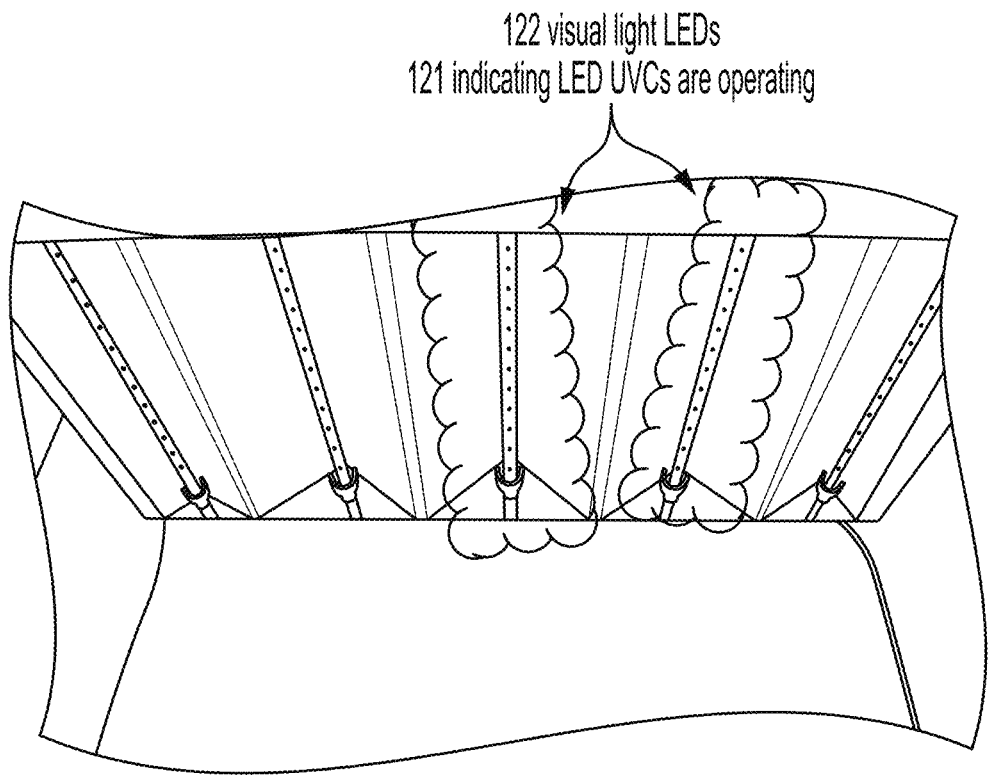
FIGS. 10A and 10B are perspective views of the disinfection chamber of FIG. 4 illustrating an LED fixture positioned at the ceiling of the disinfection chamber in accordance with the present invention.
Figure 10B:
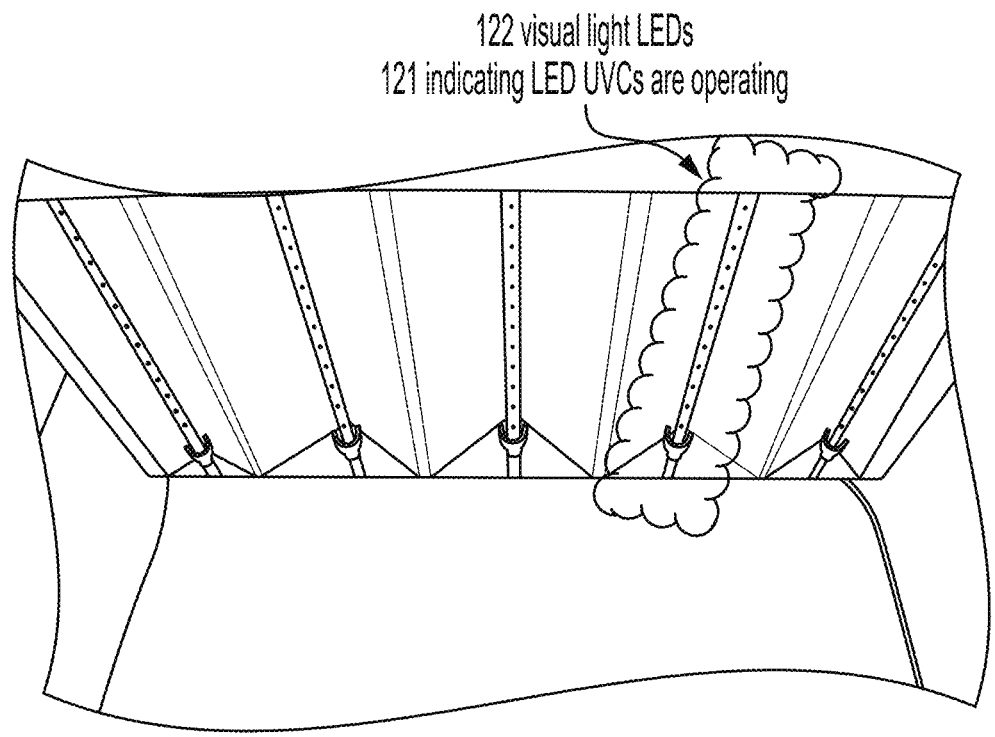

FIGS. 10A and 10B illustrate LED arrays 108 of an LED fixture 102, 104. In FIGS. 10A and 10B, LED light sources 122 emitting visible light are emitting providing a visual indication (which under normal operating perimeters would be unseen, hidden within the closed-up interior of the disinfection chamber) that the ultraviolet source 121 is emitting during a disinfection cycle. FIGS. 13C and 13E also illustrate similar LED light sources 122 emitting visible light to indicate whether LED UVC devices 121 on the LED array 108 are emitting.

FIGS. 13A, 14, 15, 16A, and 16B illustrate LED arrays 108 with LED light sources 122 emitting visible light that may be used as work lights. For example, these "work light" LEDs 122 on the LED arrays 108 may be used when the disinfection chamber's door 404 is open and objects 120 are being taken out of the chamber 400, or additional objects 120 are being placed into the chamber 400 for a disinfection cycle. FIGS. 4-6, 8, and 9 illustrates objects 120 placed onto a grill framework 112 within the interior space of an exemplary disinfection chamber 400.

Figure 11A:
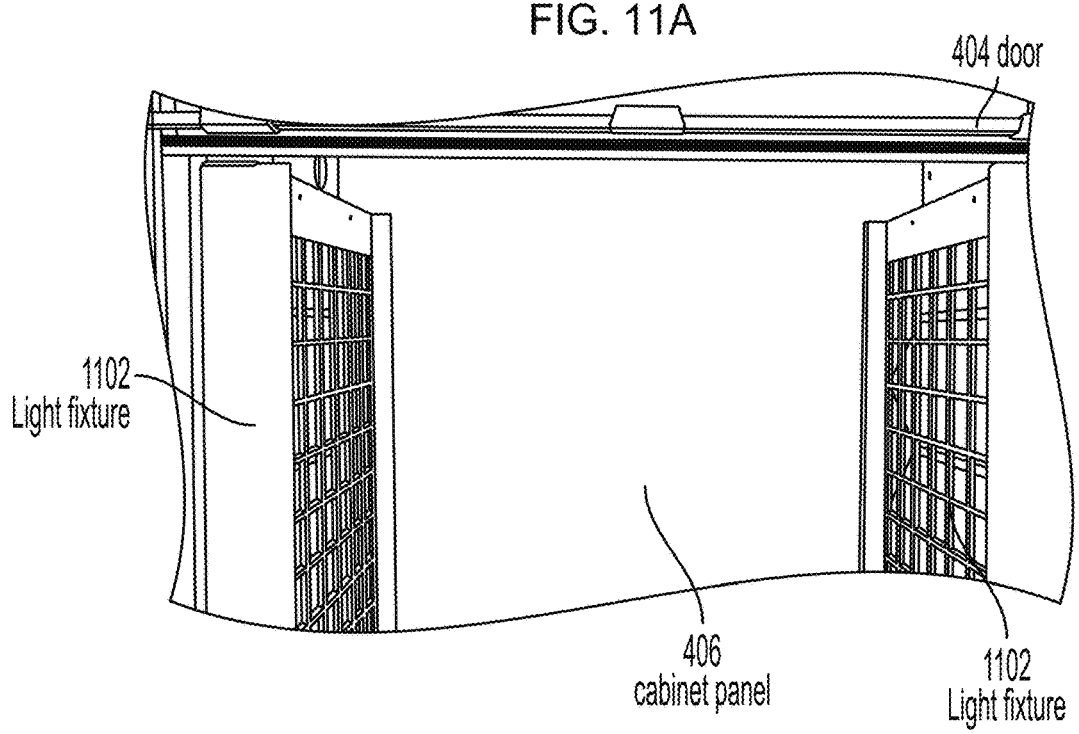
FIGS. 11A and 11B are perspective views of an alternative disinfection chamber illustrating LED fixtures arranged on either side of the disinfection chamber.
Figure 11B:
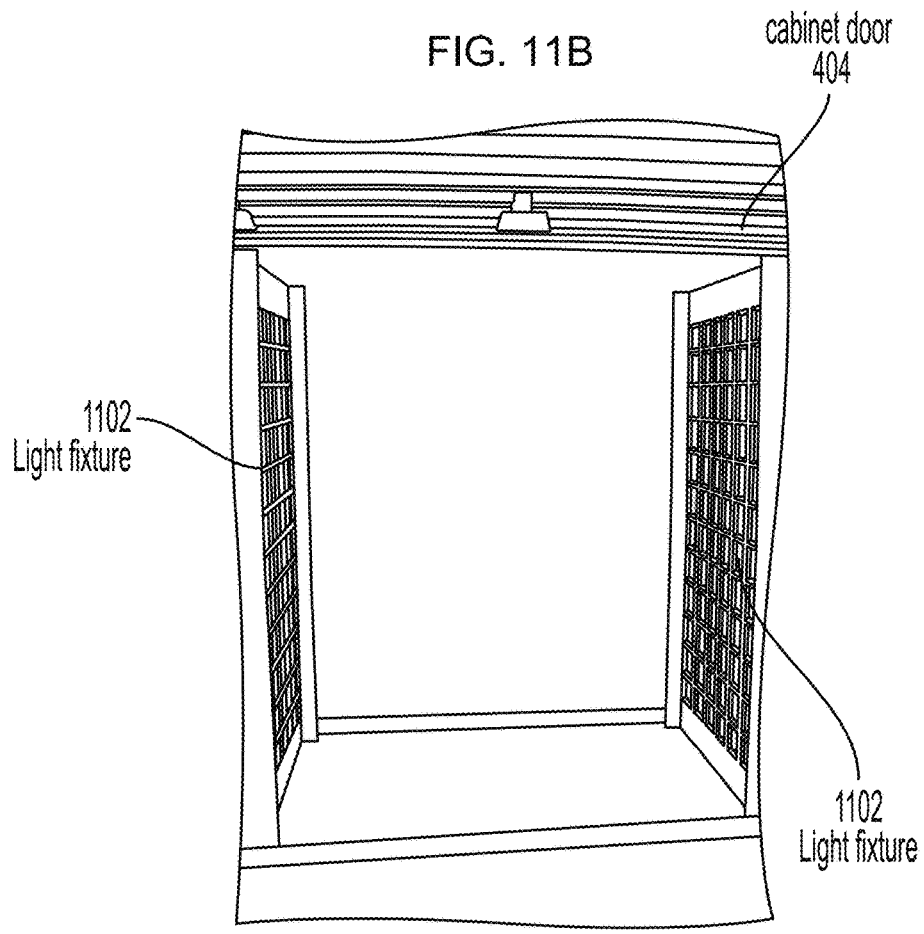

FIGS. 11A and 11B illustrate an alternative disinfection chamber 500. As illustrated in FIGS. 11A and 11B, LED fixtures 1102 are arranged vertically on either side of the chamber 500. The light fixtures 1102 are similar to the light fixtures 102*a*, 102*b* arranged on the top and bottom of disinfection chamber 100 (see FIG. 1). While not illustrated in FIGS. 11A and 11B, an exemplary disinfection chamber 500 may also include additional light fixtures arranged on the floor and ceiling of the chamber 500, such that objects placed within the interior space of the chamber 500 are surrounded by ultraviolet sources above, below, and on either side.

FIGS. 12A, 12B, 16A, and 16B illustrate close-up views of an exemplary LED array 108 of a light fixture 102, 104, 1102. As discussed herein, each LED array 108 is positioned within the W-shaped reflector's (302) respective valleys or troughs 306 within the LED fixture 102, 104, 1102. As discussed herein, the W-shaped reflector 302 is configured to achieve a desired fluency or UV dose to be received by an object placed within the disinfection chamber. Each LED array 108 includes both LED ultraviolet sources 121, and LED visible light sources 122. The LED visible light sources 122 may include both "white light" LED light sources for use as a work light, as well as a colored light LED light source to be used as an ultraviolet light indicator light. As seen in FIGS. 12A, 12B, 16A, and 16B, the LED ultraviolet sources 121 (e.g., LED UVC), and the LED visible light sources 122 are arranged on the LED array 108 in an alternating fashion.

Figure 13A:
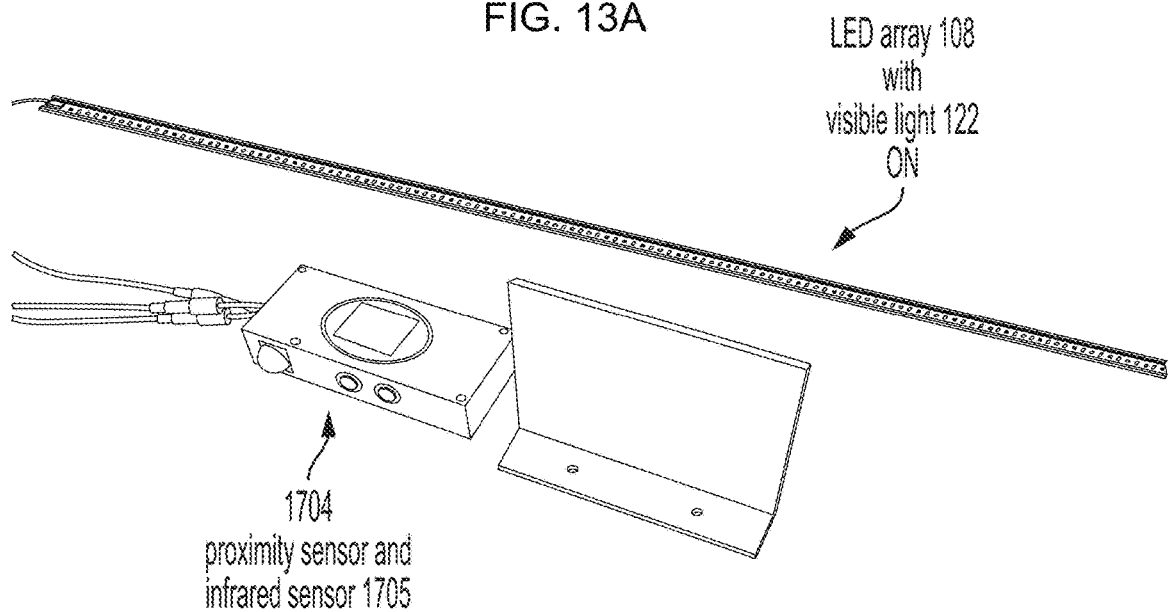
FIGS. 13A-13E are perspective views of a linear array of LED devices illustrating the operation of an occupancy detector and infrared sensor in accordance with the present invention.
Figure 13B:
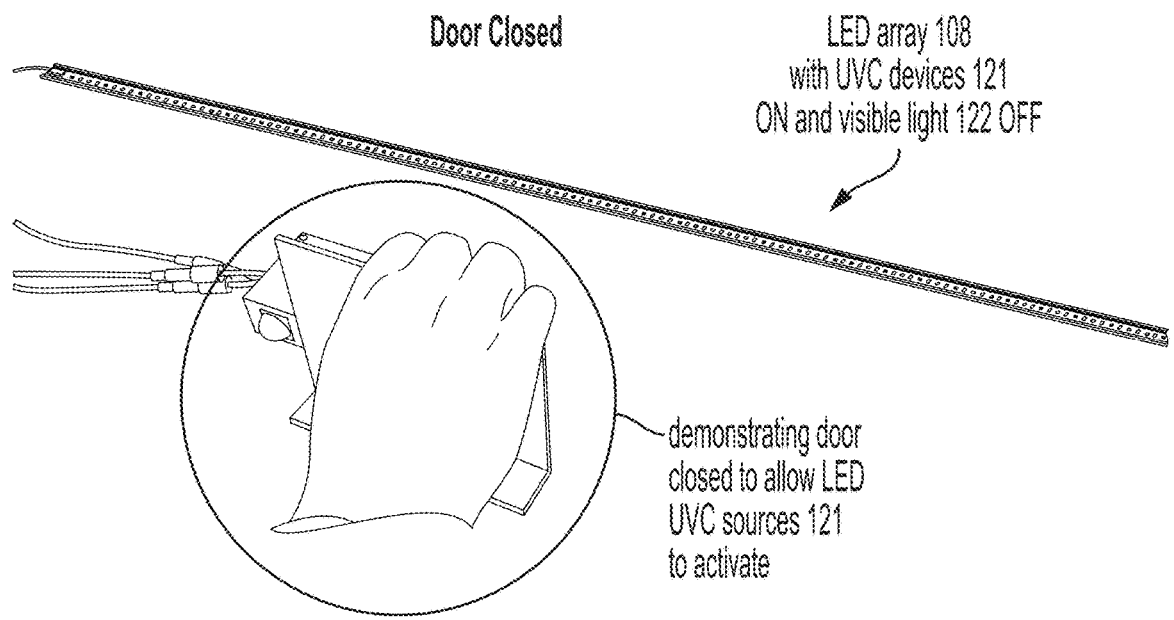
Figure 13C:
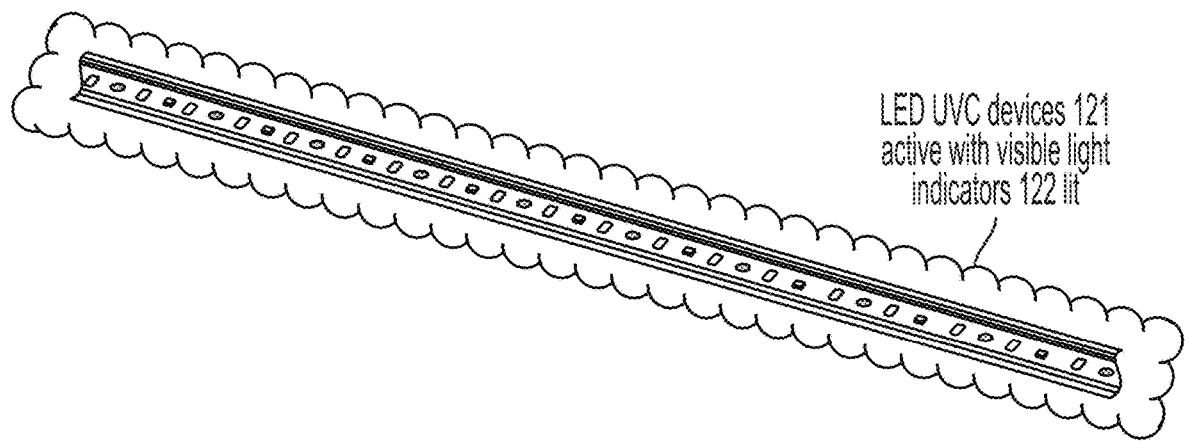
Figure 13D:
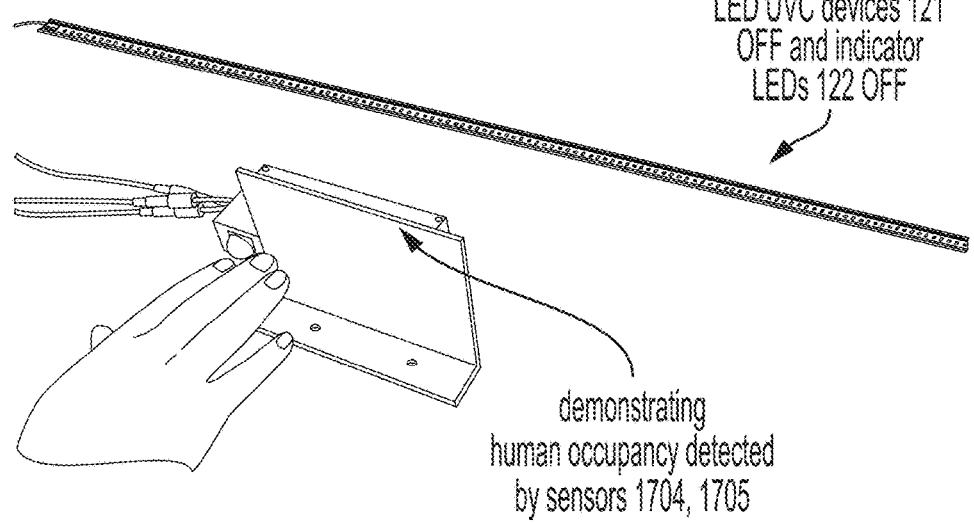
Figure 13E:
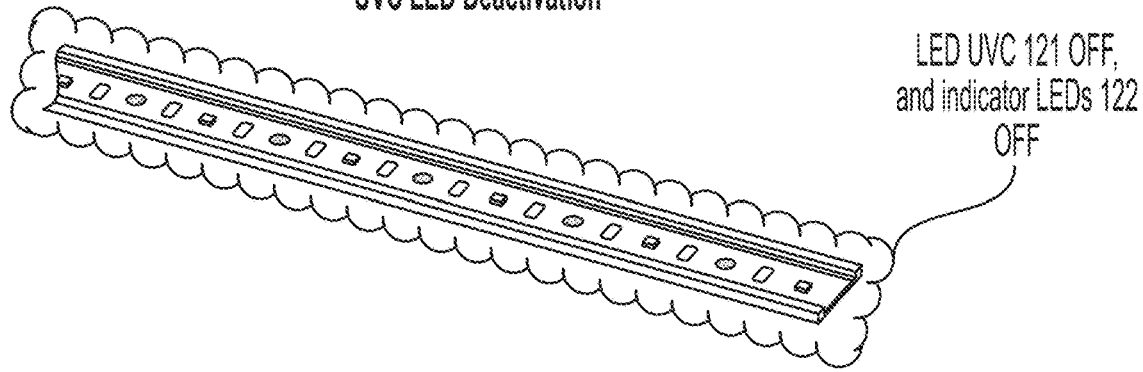
Figure 14:
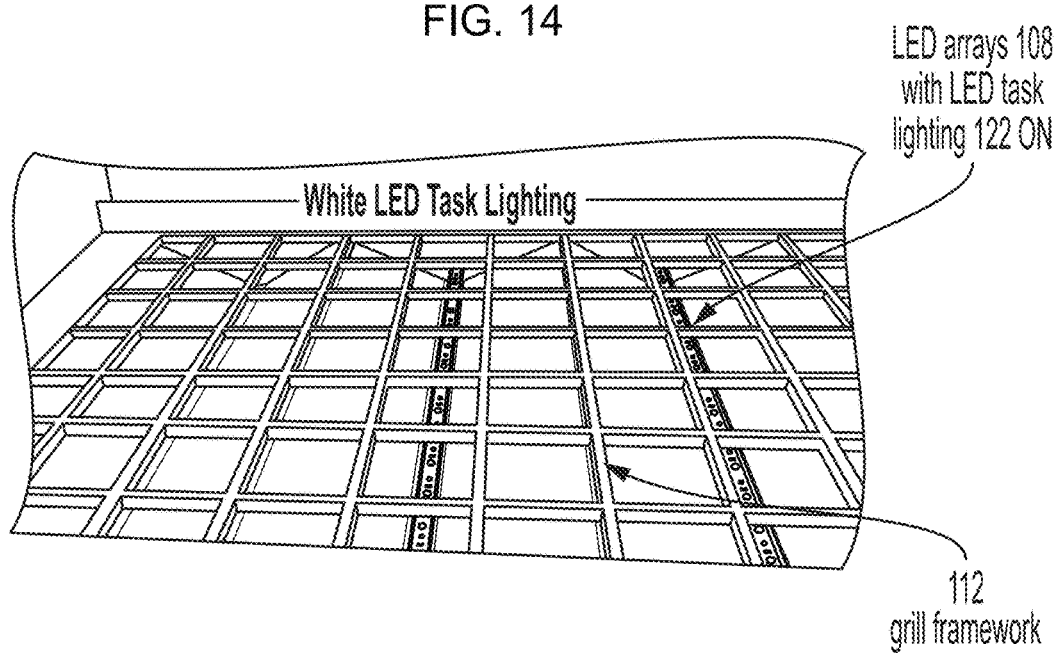
FIGS. 14 and 15 are perspective views of one of the LED fixtures of the disinfection chamber of FIG. 4 illustrating the operation of LED visible light sources in accordance with the present invention.
Figure 15:
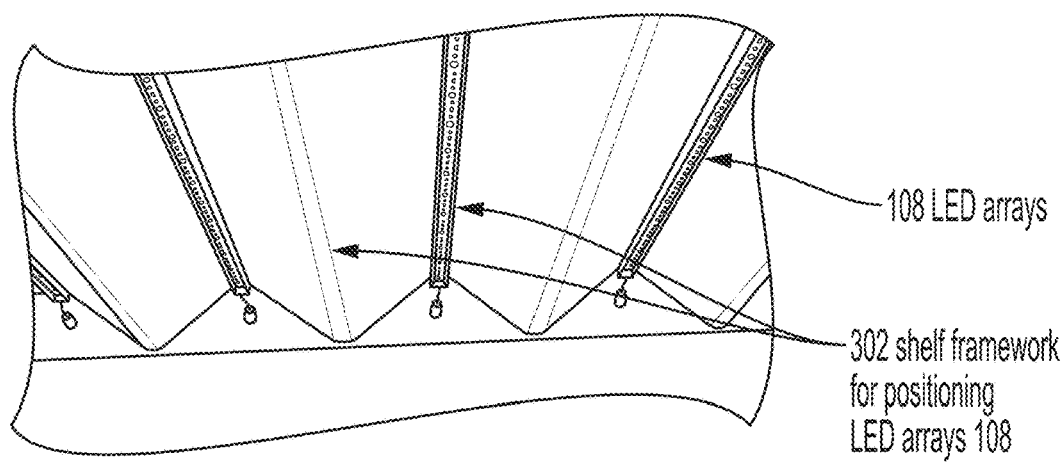
Figure 16A:
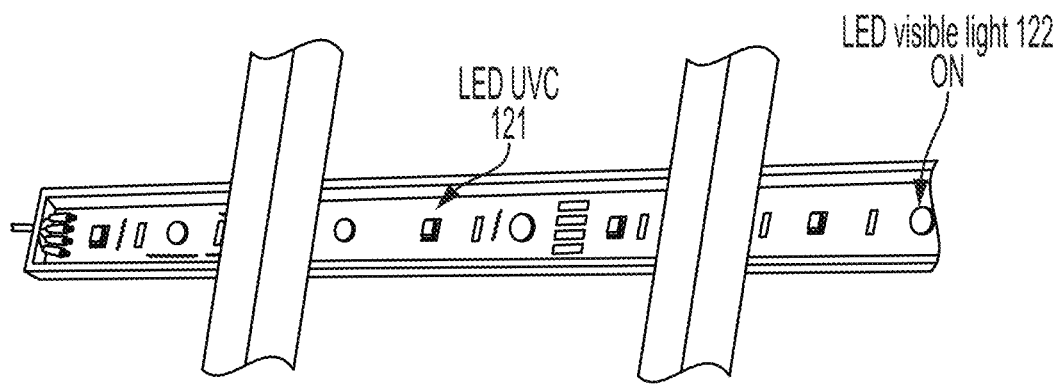
FIGS. 16A and 16B are perspective views of a portion of one of the LED fixtures of the disinfection chamber of FIG. 4 illustrating a linear array of LED devices including LED visible light sources and LED ultraviolet sources.
Figure 16B:
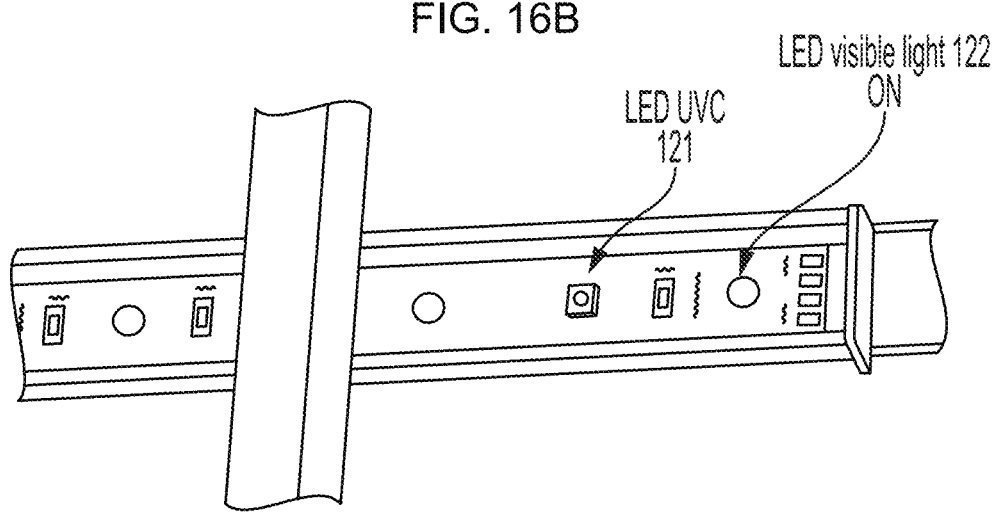

FIGS. 13A, 13B, 13C, and 13D illustrate the operation of the occupancy and infrared sensors 1704a-n, 1705a-n communicatively coupled to a control module 1702 of the disinfection chamber (see FIG. 17). As illustrated in FIG. 13A, when the proximity sensor 1704 detects that the "door" of the chamber is open, only the visible light, "work light," LEDs 122 will be emitting. While FIGS. 13A-13D illustrate a single combined proximity sensor 1704 and infrared sensor 1705, the disinfection chamber may have any number of sensors 1704a-n, 1705a-n. In an exemplary disinfection chamber, a pair of proximity sensors 1704a, 1704b are arranged on opposite sides of the chamber to detect the presence or absence of the door (see FIG. 17). The exemplary disinfection chamber may also include at least one infrared sensor 1705a positioned to detect the motion of a person near the open chamber. The infrared sensor 1705a provides a fail-safe against inadvertently initiating a disinfection cycle should both proximity sensors 1704a, 1704b incorrectly detect the presence of the chamber door (e.g., if both proximity sensors 1704a, 1704b are blocked or detect something or someone near the opening, the proximity sensors 1704a, 1704b may incorrectly indicate the presence of the chamber door). FIG. 13B illustrates a situation when the door of the chamber has been closed. As illustrated in FIG. 13B, the visible light LEDs 122 are no longer emitting and the ultraviolet sources 121 are allowed to emit (as controlled by the control module 1702). The control module 1702 of FIG. 17 allows the ultraviolet sources 121 to emit when the one or more proximity sensors (e.g., sensor 1704a and sensor 1704b) detect the presence of the door. As illustrated in FIG. 13C, when the LED ultraviolet sources 121 are emitting, visible light LEDs 122 used as indicator lights may also be emitting. As illustrated in FIGS. 13A and 13B, when the proximity sensors 1704 detect that the door is open, the disinfection chamber is unable to begin a disinfection cycle. As illustrated in FIG. 13D, when a human has been detected by the infrared sensor 1705 located within the interior space of the chamber, the control module 1702 will stop the LED ultraviolet source 121 from emitting. The infrared sensor 1705 is a safety override to provide a further protection against the ultraviolet source 121 from emitting when the door is still open. In other words, even if a person is positioned close enough to the disinfection chamber that the proximity sensors (e.g., sensor 1704a and sensor 1704b) detect the presence of the door, the infrared sensor 1705a would detect the presence of the person.

While the light fixtures 102, 104, 1102 illustrated herein utilize LED light arrays 108, alternative disinfection chambers may utilize one or more ultraviolet sources configured to emit ultraviolet C (UV-C) light in a selected disinfecting or germicidal wavelength ranging from 222 nm to 280 nm, e.g., 222 nm and 254 nm. The ultraviolet sources (121) and the visible light sources (122) are energized when they receive power through a wiring harness that is arranged within each of the LED arrays 108 of the disinfection chamber. The disinfection chamber is powered by a low voltage power source 1706, for example, 12 VDC, 24 VDC (see FIG. 17). In some embodiments, an exemplary disinfection chamber may be powered by a power source 1706 that is a high-voltage power source, such as, 120 VAC, and 240 VAC. As discussed herein, the control module 1702 of the disinfection chamber is configured to control the operation of the ultraviolet source 121 and the visible light sources 122 via the wiring harnesses of the LED arrays 108.

Figure 7:
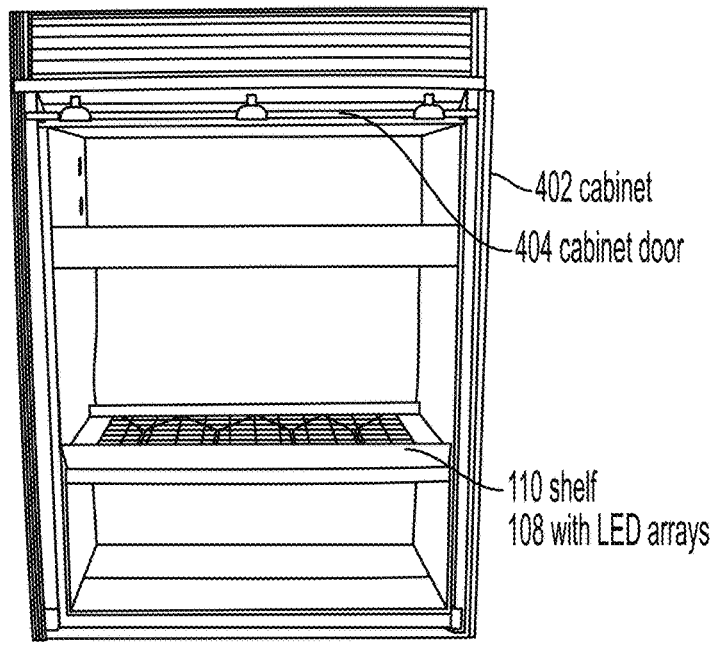
Figure 8:
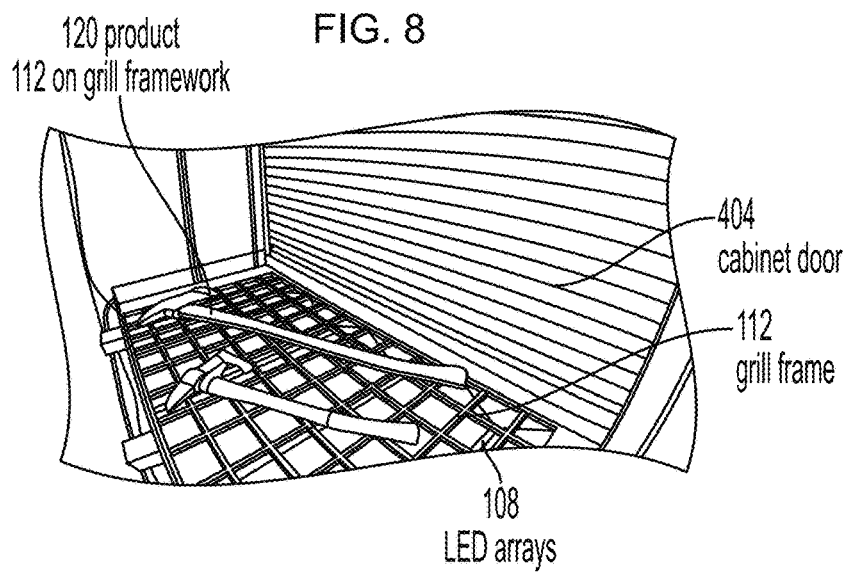

As illustrated in FIG. 7, the disinfection chamber may be configured as a deployable, standalone unit. Alternatively, the disinfection chamber may be configured for placement in an interior space of a vehicle. An exemplary disinfection chamber is considered "standalone" when it is configured as a freestanding unit and not contained or confined within a space. As discussed herein, the exemplary disinfection chamber, whether standalone units, or configured for placement in a confined space, the disinfection chamber is configured to be powered via a low-voltage DC power source.

FIG. 17 illustrates a block diagram of a disinfecting antimicrobial system (such as the disinfection chamber discussed herein), that includes a control module 1702 for controlling the operation of light fixtures 1708a-n and their LED arrays 108. Similar to those discussed herein, the LED arrays 108 include ultraviolet sources 121 arranged to provide ultraviolet sanitation of exposed surfaces of objects placed within the interior of the disinfection chamber. As controlled by the control module 1702, the ultraviolet sources 121 of the LED arrays 108 of the light fixtures 1708a-n are instructed to enter a disinfection cycle and to emit ultraviolet light so long as the proximity sensors (e.g., sensor 1704a, sensor 1704b) detect the presence of a door enclosing the interior of the chamber, and so long as the infrared sensor (e.g., sensor 1705a) does not detect the presence of a person. As discussed herein, when the infrared sensor 1705a detects the presence of a person, the door is determined to be opened and the control module 1702 will not initiate the disinfection cycle. As discussed herein, when the door is open, the "task lights" 122 will be emitting. As also discussed herein, when the ultraviolet sources 121 are emitting, LEDs 122 emitting visible light may also be energized.

Figure 18:
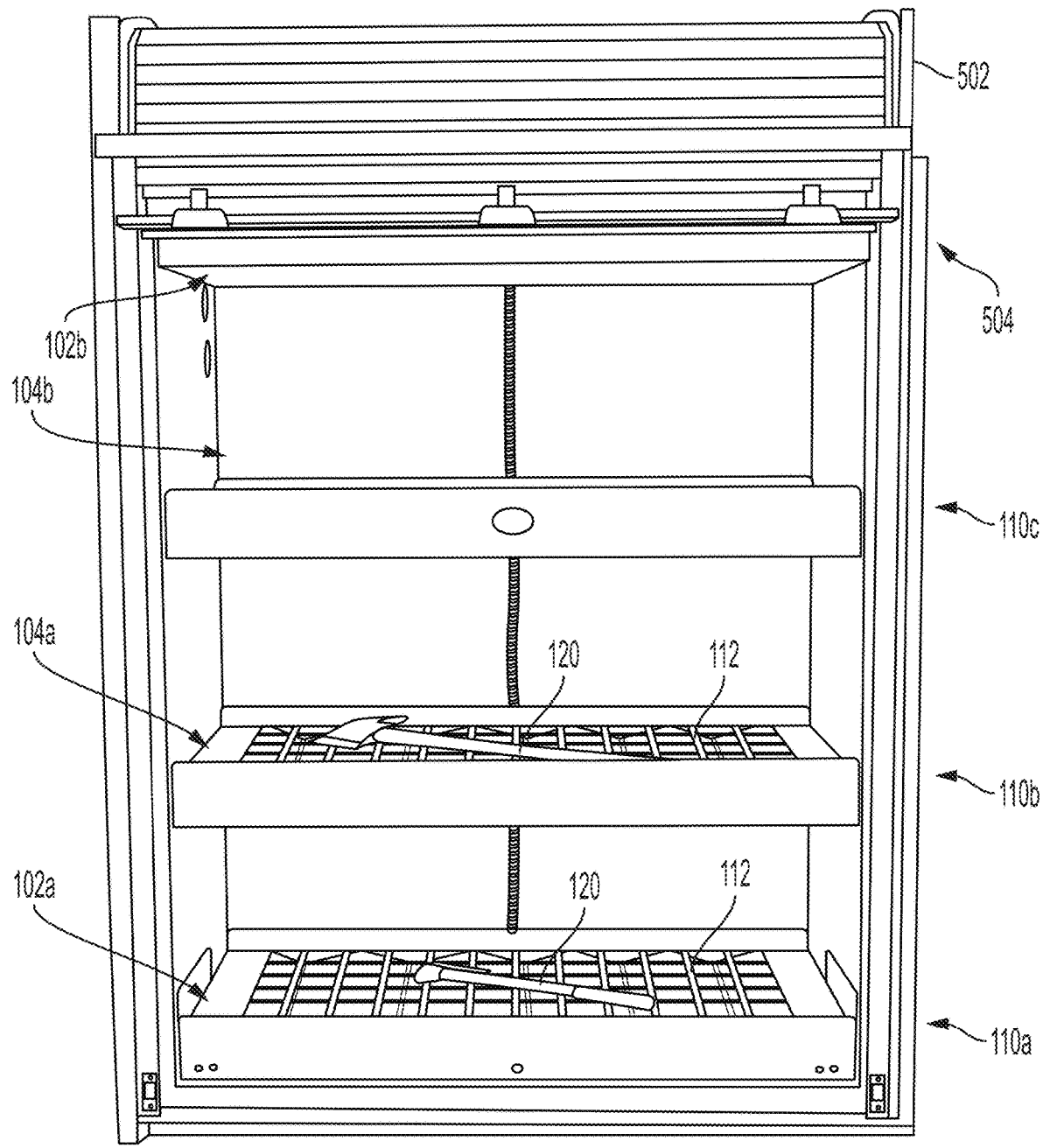
FIG. 18 a perspective view of an alternative disinfection chamber illustrating multiple adjustable shelves in accordance with the present invention.
Figure 19A:
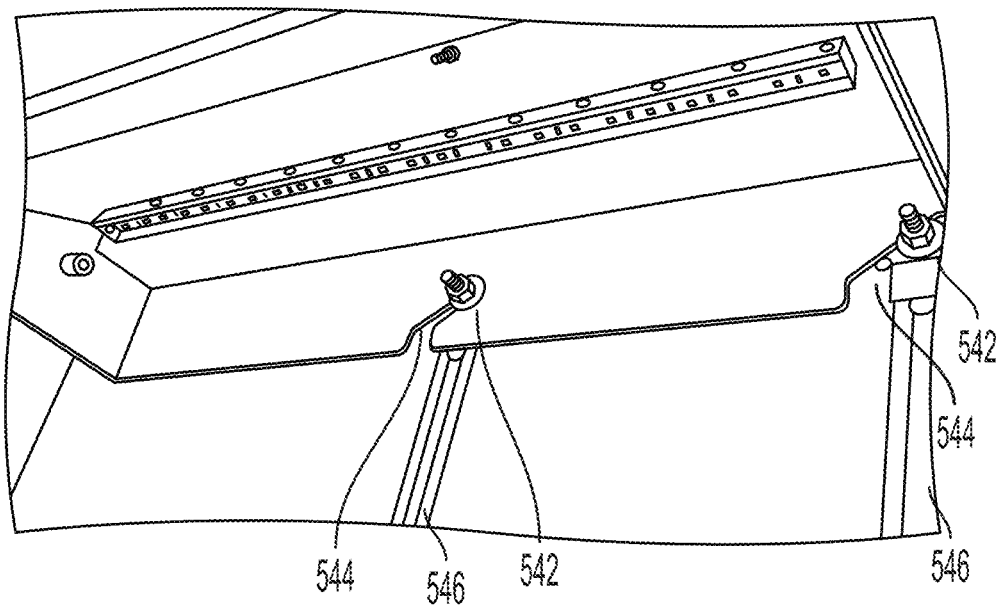
FIG. 19A is a perspective view of the underside of a shelf of the disinfection chamber of FIG. 18 illustrating grooves and mounting hardware.
Figure 19B:
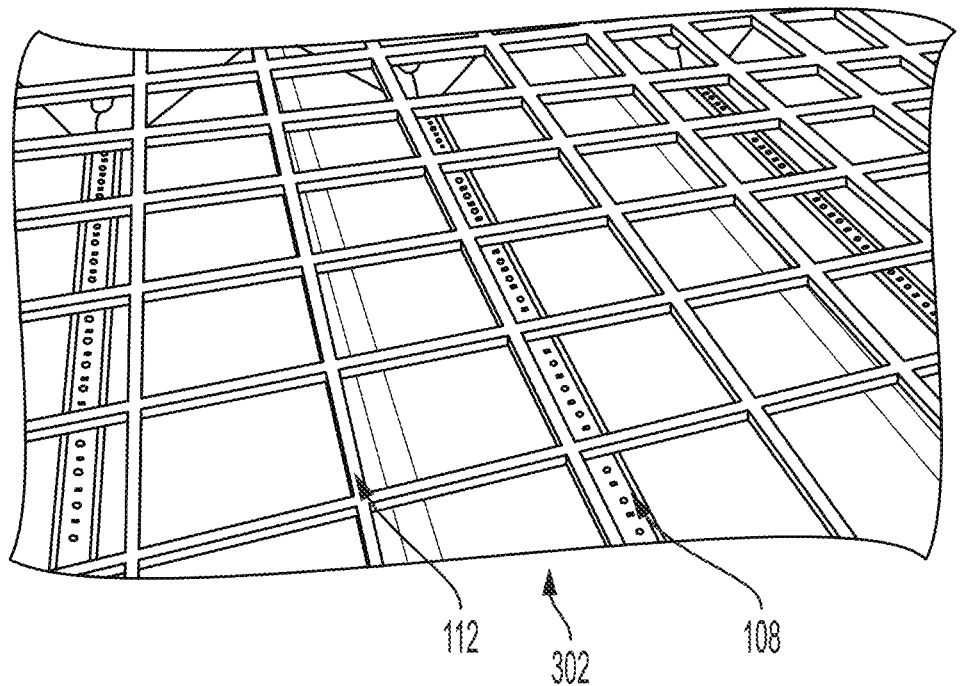
FIG. 19B is a perspective view of the topside of the shelf of FIG. 19A illustrating an exemplary grating.

Referring to FIGS. 18, 19A, and 19B, an alternative disinfection chamber 500 includes one or more adjustable-height shelves 510. Like the disinfection chamber 400, illustrated in FIG. 4, the disinfection chamber 500 includes a housing 502 with a door 504. The door 504 may be a roll-down door or some other suitable door providing access to the interior of the disinfection chamber 500. The disinfection chamber 500 includes a lower light fixture 102a with an arrangement of LED light arrays 108, and an upper light fixture 102b with another arrangement of LED light arrays 108. The disinfection chamber also includes a set of shelves 110a-c: a lower shelf 110a formed of the lower light fixture 102a and a grid framework 112; a second shelf 110b formed of a light fixture 104a and a grid framework 112; and a third shelf 110c formed of another light fixture 104b and another grid framework 112. As illustrated in FIG. 19A, the second shelf 110*b* and the third shelf 110*c* are held at a selected height by use of an arrangement of fasteners 542 (via slots 544 in the light fixture 104) which slide up and down within channels 546. Each light fixture 104 includes a pair of slots 544 on either side which line up with the channels 546. Tightening down the fasteners 542 will hold the light fixture 104 at a selected height within the disinfection chamber 500.

Figure 5:
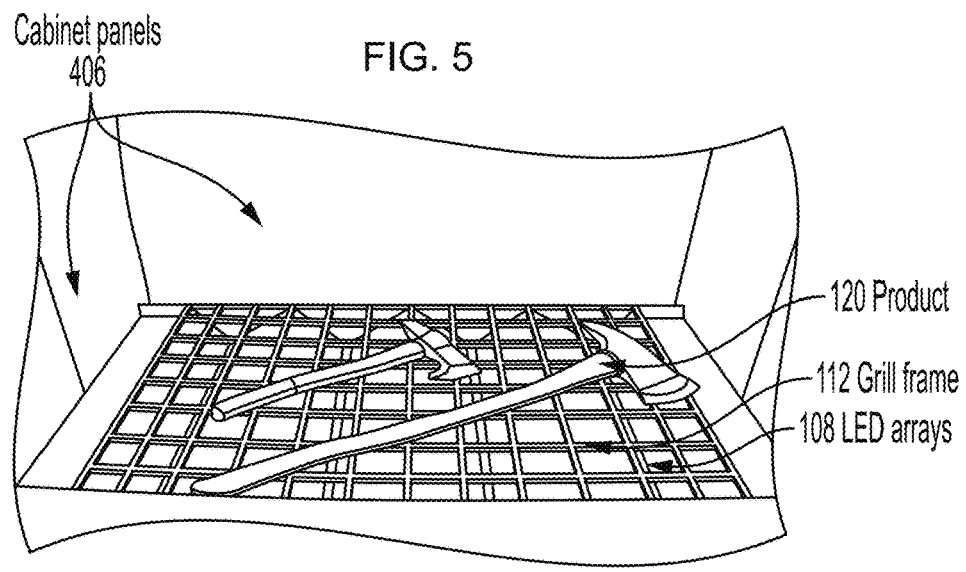
FIGS. 5-9 are additional perspective views of the interior of the disinfection chamber of FIG. 4.
Figure 6:
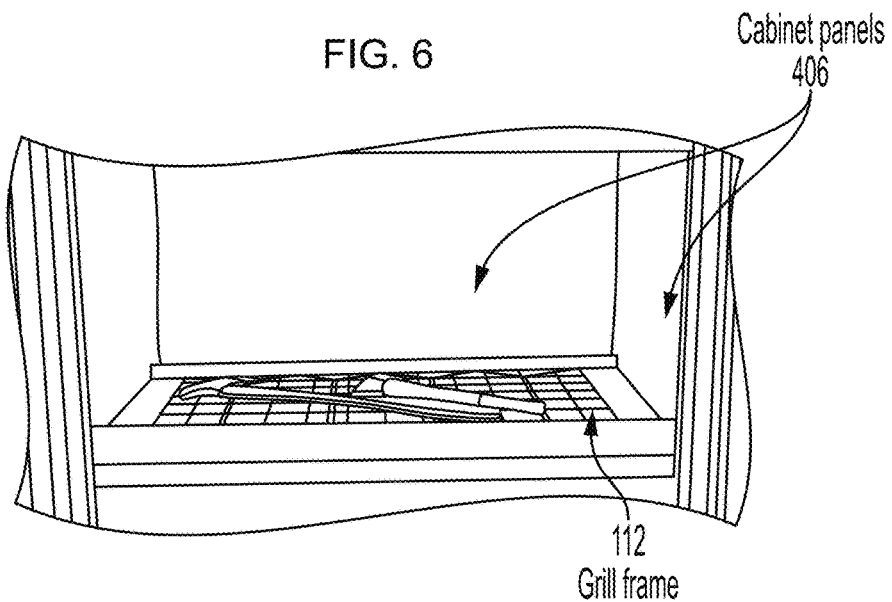
Figure 9:
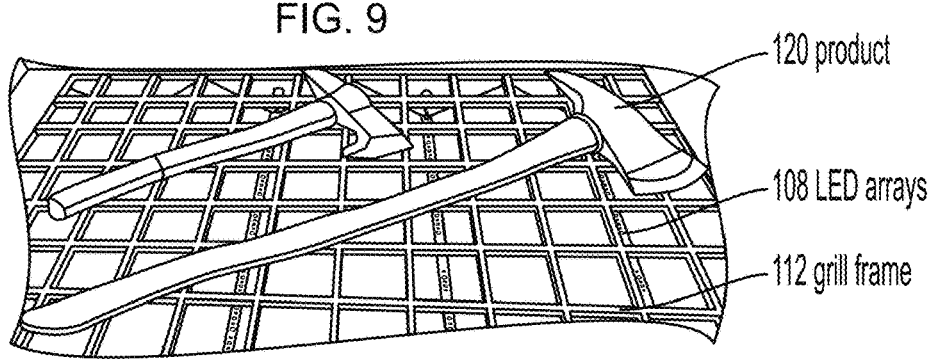

Like the disinfection chamber 400 illustrated in FIGS. 5 and 9, and depicted in FIG. 19B, the disinfection chamber 500 includes LED light arrays 108 arranged in valley or troughs 306 of W-shaped reflectors 302 of the light fixtures 102, 104. FIG. 19B illustrates the placement of the grill framework 112 overlaying the light fixture 102, 104.

Figure 4:
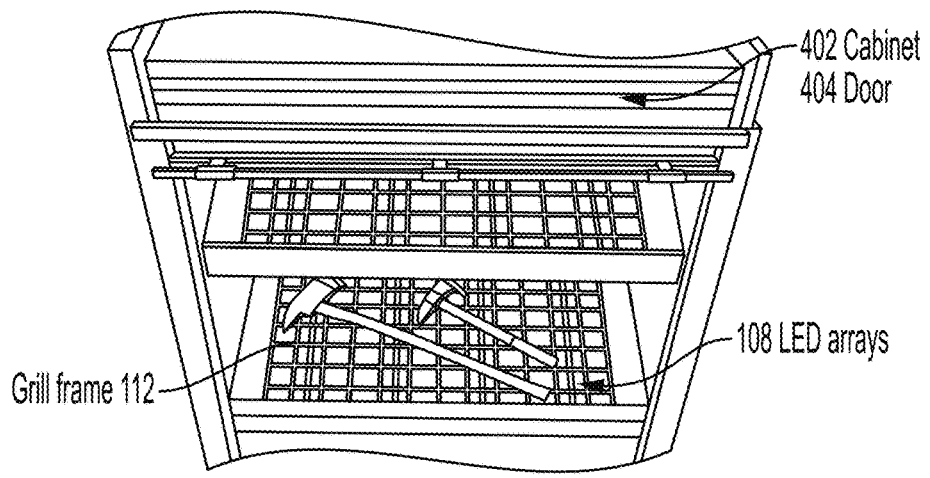
FIG. 4 is a perspective view of an interior of an exemplary disinfection chamber illustrating objects placed upon a shelf within the interior space of the disinfection chamber in accordance with the present invention.
Figure 20:
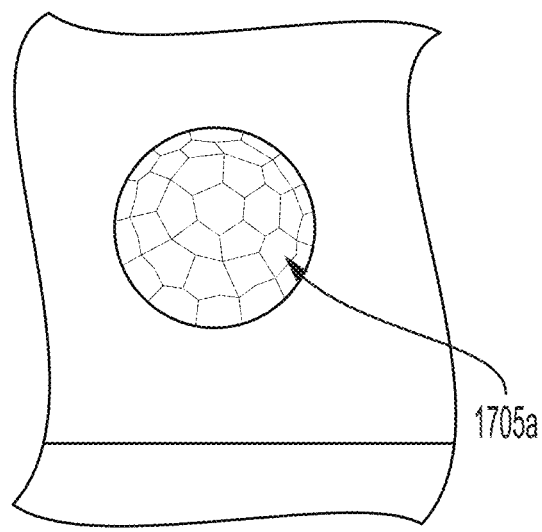
FIG. 20 is a perspective view of an exemplary passive infrared sensor for detecting the presence of humans when the door of the disinfection chamber is open in accordance with the present invention.
Figure 21:
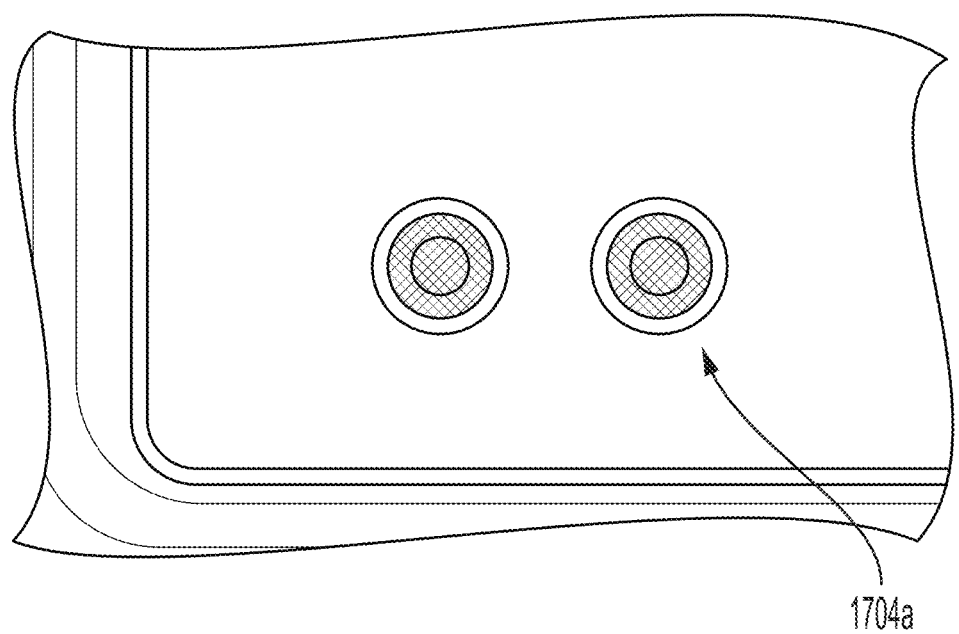
FIG. 21 is a perspective view of an exemplary ultrasonic proximity sensor for detecting whether the door of the disinfection chamber is open or closed in accordance with the present invention.

FIGS. 20 and 21 illustrate exemplary sensors 1704, 1705 for use in a disinfection chamber 400, 500 (see FIGS. 4 and 18). FIG. 21 depicts an arrangement of a proximity sensor 1704*a* and an exemplary placement of the ultrasonic transmitter and receiver of the proximity sensor 1704*a*. One or more proximity sensors 1704*a-n* may be arranged within a disinfection chamber 400, 500 to allow for the accurate detection of the presence or absence of the cabinet door 404, 504. As discussed herein, the disinfection chamber 400, 500 will not start a disinfection sequence until its proximity sensors 1704*a-n* have indicated that the associated door 404, 504 is in place.

With respect to FIG. 20, an exemplary passive infrared sensor 1705*a* may be positioned within the disinfection chamber 400, 500 as an additional safety device to ensure the door 404, 504 is closed. As discussed herein, should the proximity sensors 1704*a-n* incorrectly indicate that the door 404, 504 is closed (e.g., due to the close proximity of a human causing the proximity sensors 1704*a-n* to incorrectly detect the human as the door 404, 504), the addition of a passive infrared sensor 1705*a* can be used to verify that a human is not present and that the door 404, 504 is in fact closed.

Thus, ultraviolet sources (e.g., arrays of LED ultraviolet sources) may be arranged in a portable/mobile disinfection chamber. The disinfection chamber may be configured as either a freestanding, standalone unit, or as an adjustable-height cabinet for placement within a variety of different spaces. The disinfection chamber is powered by a low-voltage DC power source, such as a 12V DC power source, a battery, or a high-voltage AC power source. Light fixtures with arrays of LED ultraviolet sources and LED visible light sources may be arranged on the floor and ceiling of the interior space of the disinfection chamber, with additional LED fixtures arranged on one or more walls of the chamber. Additional shelves may be placed within the interior space of the chamber, with light fixtures arranged on the top and bottom of each of the additional shelves. The disinfection chamber is controlled by a control module that is communicatively coupled to at least one proximity sensor and at least one infrared sensor. The proximity sensors and the infrared sensors are configured to detect the presence of a door of the disinfection chamber and to detect the presence of a human, respectively. Thus, the sensors prevent the disinfection chamber from entering a disinfection cycle when the door is open and/or a human has been detected by an infrared sensor positioned within the interior of the disinfection chamber.

Changes and modifications in the specifically-described embodiments can be carried out without departing from the principles of the present invention which is intended to be limited only by the scope of the appended claims, as interpreted according to the principles of patent law including the doctrine of equivalents.

The invention claimed is:

1. A disinfection chamber for disinfecting objects placed within an interior space of the disinfection chamber, the disinfection chamber comprising:
   a plurality of LED fixtures, each comprising LED ultraviolet sources and at least one LED visible light source, wherein the LED ultraviolet sources are configured to emit germicidal ultraviolet light;
   one or more horizontally orientated shelves, each comprising a grill frame configured to support and position objects placed within the interior space of the disinfection chamber;
   wherein a first shelf of the one or more shelves is positioned at or near a floor of the interior space of the disinfection chamber, wherein the first shelf comprises a first LED fixture of the plurality of LED fixtures, wherein the first LED fixture comprises a first W-shaped reflector comprising a series of alternating peaks and valleys, wherein LED ultraviolet sources of the first LED fixture are arranged in the valleys on one side of the first W-shaped reflector, and wherein the grill frame of the first shelf is positioned above the first LED fixture;
   wherein a second LED fixture of the plurality of LED fixtures is positioned at or near a ceiling of the interior space of the disinfection chamber, wherein the second LED fixture comprises a second W-shaped reflector comprising a series of alternating peaks and valleys, wherein LED ultraviolet sources of the second LED fixture are arranged in the valleys on one side of the second W-shaped reflector; and
   wherein the first and second LED fixtures are arranged within the interior space of the disinfection chamber such that objects placed within the interior space of the disinfection chamber will be exposed from above and below to the ultraviolet sources for disinfection.

2. The disinfection chamber of claim 1, wherein the emitted ultraviolet light is ultraviolet C light.

3. The disinfection chamber of claim 1 comprising a control module and a plurality of sensors comprising at least one proximity sensor and at least one infrared sensor, wherein the control module is communicatively coupled to the LED fixtures and is configured to control the operation of the disinfection chamber such that the LED fixtures will only emit ultraviolet light when the proximity sensors detect that a door of the disinfection chamber is closed, and wherein the control module is configured to prevent the LED fixtures from emitting ultraviolet light when the infrared sensors detect the presence of a human.

4. The disinfection chamber of claim 3, wherein the at least one proximity sensor is an ultrasonic proximity sensor.

5. The disinfection chamber of claim 3, wherein the at least one proximity sensor comprises a pair of proximity sensors arranged on opposite sides of the interior space of the disinfection chamber.

6. The disinfection chamber of claim 3, wherein the at least one infrared sensor comprises a first infrared sensor positioned within the interior space of the disinfection chamber, and wherein the first infrared sensor is a passive infrared sensor.

7. The disinfection chamber of claim 6, wherein the low-voltage DC power source is one of a 12V DC power source or a 24V DC power source.

8. The disinfection chamber of claim 1, wherein the LED fixtures are powered by a low-voltage DC power source.

9. The disinfection chamber of claim 1, wherein the LED fixtures are powered by a high-voltage power source.

10. The disinfection chamber of claim 9, wherein the high-voltage power source is a 120 VAC power source or a 240 VAC power source.

11. The disinfection chamber of claim 1, wherein the disinfection chamber is configured for mounting within one of a standalone housing unit and an adjustable-height housing apparatus for mounting within a space.

12. The disinfection chamber of claim 1, wherein a second shelf of a plurality of shelves includes mounting hardware for adjustably mounting the second shelf in a selected horizontal position between the first LED light fixture and the second LED light fixture, wherein the second shelf comprises a third LED light fixture, wherein the third LED fixture comprises a third W-shaped reflector comprising a series of alternating peaks and valleys, and wherein the third LED light fixture is double-sided with opposing pairs of LED ultraviolet sources and LED visible light sources arranged on opposite sides of the third LED light fixture such that the opposing pairs of LED ultraviolet sources of the third LED light fixture are arranged in respective valleys on opposite sides of the W-shaped reflector to emit ultraviolet light above and below the second shelf.

13. The disinfection chamber of claim 1, wherein a pair of LED fixtures of the plurality of LED fixtures are arranged on opposing sides of the disinfection chamber and each configured to extend from opposing ends of the first LED fixture to opposing ends of the second LED fixture.

14. A portable disinfection chamber for disinfecting objects placed within an interior space of the disinfection chamber, the disinfection chamber comprising:
- one or more horizontally orientated shelves, each comprising a grill frame configured to support and position objects placed within the interior space of the disinfection chamber, wherein each shelf comprises a respective LED fixture positioned behind the respective grill frame;
- a second LED fixture positioned at or near a ceiling of the interior space of the disinfection chamber, wherein the second LED fixture comprises a second W-shaped reflector comprising a series of alternating peaks and valleys; and
- a plurality of sensors and a control module configured to control the LED fixtures as defined by outputs of the sensors;
- wherein each LED fixture comprises LED ultraviolet sources and LED visible light sources, wherein LED ultraviolet sources of the second LED fixture are arranged in the valleys on one side of the second W-shaped reflector, and wherein the LED ultraviolet sources are configured to emit germicidal ultraviolet light;
- wherein a first shelf of the one or more shelves is positioned at or near a floor of the interior space of the disinfection chamber, wherein the first shelf comprises a first LED fixture comprising a first W-shaped reflector comprising a series of alternating peaks and valleys, wherein LED ultraviolet sources of the first LED fixture are arranged in the valleys on one side of the first W-shaped reflector; and
- wherein the first LED fixture of the first shelf and the second LED fixture are arranged within the interior space of the disinfection chamber such that objects placed within the interior space of the disinfection chamber will be exposed from above and below to the ultraviolet sources for disinfection.

15. The portable disinfection chamber of claim 14 further comprising a cabinet configured to allow the portable disinfection chamber to be free-standing.

16. The portable disinfection chamber of claim 15 further comprising a power source configured to power the LED fixtures, wherein the power source is a low-voltage DC power source configured as either a 12V DC power source or a 24V DC power source, and wherein the power source is a battery.

17. The portable disinfection chamber of claim 14 further comprising a cabinet configured to fit into an equipment space of a vehicle.

18. The portable disinfection chamber of claim 17 further comprising a power source configured to power the LED fixtures, wherein the power source is a low-power DC power source configured as either a 12V DC power source or a 24V DC power source, and wherein the power source is coupled to a battery of the vehicle.

19. The portable disinfection chamber of claim 14, wherein the plurality of sensors comprises at least one proximity sensor and at least one infrared sensor.

20. The portable disinfection chamber of claim 19, wherein the control module is configured to prevent the LED fixtures from emitting ultraviolet light when either the infrared sensor detects the presence of a human, or the proximity sensor fails to detect the presence of a chamber door.

* * * * *